(12) United States Patent
Nielsen et al.

(10) Patent No.: US 7,722,915 B2
(45) Date of Patent: May 25, 2010

(54) PREPARATION OF HYDROPHILLIC COATINGS UTILIZING A 1,3-DIOXOLANE COMPOUND

(75) Inventors: Bo Rud Nielsen, Alleroed (DK); Niels Joergen Madsen, Alleroad (DK)

(73) Assignee: Coloplast A/S, Humlebaek (DK)

( * ) Notice: Subject to any disclaimer, the term of this patent is extended or adjusted under 35 U.S.C. 154(b) by 379 days.

(21) Appl. No.: 11/631,810

(22) PCT Filed: Jul. 6, 2005

(86) PCT No.: PCT/DK2005/000472

§ 371 (c)(1),
(2), (4) Date: Jul. 9, 2007

(87) PCT Pub. No.: WO2006/002644

PCT Pub. Date: Jan. 12, 2006

(65) Prior Publication Data

US 2007/0292595 A1    Dec. 20, 2007

(30) Foreign Application Priority Data

Jul. 7, 2004    (DK) ............................... 2004 01071

(51) Int. Cl.
*A41D 19/00*    (2006.01)
*C09K 3/00*    (2006.01)
(52) U.S. Cl. .................... 427/2.3; 252/182.12
(58) Field of Classification Search .............. 427/2.3; 252/182.11, 182.12
See application file for complete search history.

(56) References Cited

U.S. PATENT DOCUMENTS

| 3,830,920 A | 8/1974 | Morrison et al. |
| 4,842,597 A | 6/1989 | Brook |
| 5,531,715 A * | 7/1996 | Engelson et al. ............. 604/265 |
| 5,545,151 A | 8/1996 | O'Connor et al. |
| 2001/0003796 A1 | 6/2001 | Yang et al. |
| 2002/0016574 A1 | 2/2002 | Wang et al. |
| 2004/0012759 A1 | 1/2004 | Lo |
| 2005/0043715 A1 | 2/2005 | Nestenborg et al. |

FOREIGN PATENT DOCUMENTS

| EP | 0 592 870 A1 | 4/1994 |
| EP | 0 923 398 | 6/1999 |
| WO | WO 90/05162 | 5/1990 |
| WO | WO 92/19288 A1 | 11/1992 |
| WO | WO 98/11932 | 3/1998 |
| WO | WO 03/083040 A2 | 10/2003 |
| WO | WO 03/092779 A1 | 11/2003 |
| WO | WO 2004/056909 A1 | 7/2004 |

OTHER PUBLICATIONS

Anonymous: "Lubrizol Estane 58212 Ether Based Thermoplstic Polyurethane", Matweb (Product Data Sheet), 1996, (XP002561854); (retrieved from Internet: http:/www.matweb.com/search/datasheet.aspx?matguid= bf15d6b686bb4062bb63132d0cfca351).

* cited by examiner

*Primary Examiner*—Thao T. Tran
(74) *Attorney, Agent, or Firm*—Jacobson Holman PLLC

(57) ABSTRACT

A method for the preparation of a package comprising a packing means holding a medical device element of a substrate polymer, said substrate polymer having on at least a part of the surface thereof a hydrophilic coating, wherein the hydrophilic coating has been applied to the surface of said substrate polymer in the form of a solution of a hydrophilic polymer selected from the groups consisting of polyvinylpyrrolidone and polyethylene oxide in a vehicle comprising an optionally substituted 1,3-dioxolane compound, followed by evaporation of at least part of the vehicle and arranging said medical device element having the coating of the non-crosslinked hydrophilic polymer within a packing means, and sealing said packing means.

6 Claims, No Drawings

PREPARATION OF HYDROPHILLIC COATINGS UTILIZING A 1,3-DIOXOLANE COMPOUND

This is a national stage of PCT/DK2005/000472 filed 6 Jul. 2005 and published in English.

FIELD OF THE INVENTION

The present invention relates to a simplified method for the preparation of durable non-cross-linked hydrophilic coatings on medical device elements.

Thus, the present invention relates to a method for the preparation of a package comprising a packing means holding a medical device element of a substrate polymer, said substrate polymer having on at least a part of the surface thereof a hydrophilic coating. The present invention also relates to a medical device having a durable coating of a non-cross-linked hydrophilic polymer and to a package including such a medical device.

Medical devices of the nature disclosed herein have a surface having a low friction when wet, and include medical instruments and devices such as catheters, endoscopes and laryngoscopes, tubes for feeding or drainage or endotracheal use, guide wires, condoms, barrier coatings, e.g. for gloves, wound dressings, contact lenses, implants, extracorporeal blood conduits, membranes e.g. for dialysis, blood filters, and devices for circulatory assistance.

BACKGROUND OF THE INVENTION

The application of hydrophilic coatings on medical devices has become a very important method to improve biocompatibility between living tissue and the medical device. Another important property of hydrophilic coatings is to reduce the friction and to render biomedical devices slippery when wet. Medical devices like catheters, guide wires, endoscopes etc. are often sliding in direct contact with the surface of living tissue when in use. Catheters and guide wires may e.g. be introduced into the blood vessels or a catheter for catheterization of the bladder is introduced through the urethra and withdrawn later after emptying the bladder when performing catheterization or after some time when performing more or less permanent catheterization. In both applications, the medical device is sliding in direct contact with a physiological surface, the walls of the blood vessels, or the mucosa of the urethra, respectively.

There is a need for improved, in particular simplified, methods for the preparation of medical devices.

DESCRIPTION OF THE INVENTION

The present invention is based on the finding that the preparation of packages comprising medical devices having a coating of a non-cross-linked hydrophilic polymer can be simplified by utilizing 1,3-dioxolane compounds. The method of the invention is simplified compared to conventional methodology in which a hydrophilic polymer is cross-linked, and the method only requires environmentally acceptable components, i.e. reactive monomers and hazardous solvents and plasticizers are not necessary, although such solvents and plasticizers may be used in certain embodiments. Another advantage of the method of the present invention is that coating of the inner surfaces of medical devices, e.g. catheters, is rendered possible in that the coatings are not UV-cured.

Thus, the present invention provides a method for the preparation of a package comprising a packing means holding a medical device element of a substrate polymer, said substrate polymer having on at least a part of the surface thereof a hydrophilic coating, said method comprising the steps of:

(i) providing a medical device element comprising a substrate polymer selected from the group consisting of polyurethane and polyvinylchloride, (ii) providing a polymer solution comprising 0.1-20% by weight of a hydrophilic polymer selected from the groups consisting of polyvinylpyrrolidone and polyethylene oxide, 0-10% by weight of additive(s), and the balance of a vehicle, said vehicle comprising 50-100% by weight of an optionally substituted 1,3-dioxolane compound, with the proviso that the hydrophilic polymer is not polyethylene oxide when the substrate polymer is polyvinylchloride, (iii) applying said polymer solution to the surface of said substrate polymer, thereby forming a non-cross-linked hydrophilic coating on at least a part of the surface of the substrate polymer, (iv) evaporating at least a part of the vehicle, and (v) arranging said medical device element having the coating of the non-cross-linked hydrophilic polymer within a packing means, and sealing said packing means.

Medical Device Element

The term "medical device" should be interpreted in a fairly broad sense. Suitable examples of medical devices (including instruments) are catheters (such as urinary catheters), endoscopes, laryngoscopes, tubes for feeding, tubes for drainage, guide wires, condoms, urisheaths, barrier coatings e.g. for gloves, stents and other implants, extra corporeal blood conduits, membranes e.g. for dialysis, blood filters, devices for circulatory assistance, dressings for wound care, urinary bags, and ostomy bags. Most relevant are catheters, endoscopes, laryngoscopes, tubes for feeding, tubes for drainage, guide wires, and stents and other implants. Particularly interesting medical devices within the context of the present invention are catheters, such as urinary catheters.

Some medical devices may be constructed of one or more medical device elements which, when being assembled or rearranged, represent the ready-to-use medical device. Reference to a "medical device element" means the medical device as such (i.e. one piece medical device) or a part of a "ready-to-use" medical device.

Medical devices and medical device elements can be formed from a variety of types of basic materials, such as plastics, metals, glass, ceramics, etc. Typical examples of plastic materials for medical devices are polymers such as polyurethanes and copolymers thereof, or polyether block amides such as Pebax™ or other polymer materials including polyvinyl chloride, polyamide, silicone, styrene-ethylene/butylene-styrene block copolymers (SEBS), styrene-isoprene-styrene block copolymers (SIS), styrene-ethylene/propylene-styrene block copolymers (SEPS), ethylene-vinyl acetate copolymers (EVA), polyethylene (PE), metallocene-catalyzed polyethylene, and copolymers of ethylene and propylene or mixtures of such. Currently very relevant materials are polyurethanes and copolymers thereof, as well as polyvinylchloride.

In the present context, the medical device comprises at least one medical device element of a substrate polymer selected from the group consisting of polyurethane and polyvinylchloride.

Substrate Polymer

It should be understood from the above, that the substrate polymer may constitute the entire medical device, or may constitute a medical device element. The type of substrate polymer to be utilized in the context of the present invention is selected from polyurethanes and polyvinylchloride. Useful commercially available substrate polyurethanes are, e.g., Estane 58212 from Noveon, Texin 5590 from Bayer, and Elastollan 1100 from BASF. A useful, commercially available substrate polyvinylchloride is XH 76294 from Norsk Hydro.

The surface on which the hydrophilic coating is applied may be the full surface of the substrate polymer or a partial surface. In some embodiments, a part of the surface is masked with a film or the like so as to form a predetermined pattern of the hydrophilic coating on the surface.

Polymer Solution

The hydrophilic polymers to be utilized in the present context are polyvinyl pyrrolidone and polyethylene oxide, with the proviso that the hydrophilic polymer is not polyethylene oxide when the substrate polymer is polyvinylchloride. In many preferred embodiments, the hydrophilic polymer is polyvinyl pyrrolidone. Thus, the polymer solution may comprise one or more hydrophilic polymers of this type, i.e. homopolymers as well as copolymers wherein a major portion, e.g. 75% or more, of the monomer units (by weight) are selected from the group consisting of N-vinyl pyrrolidone units and ethylene oxide units. A hydrophilic copolymer may, e.g., be achieved by adding monomers of vinylic or acrylic nature to N-vinyl pyrrolidone so as to obtain copolymers of polyvinyl pyrrolidone, e.g. polyvinyl pyrrolidone-vinyl acetate copolymers.

When using the pure polyvinyl pyrrolidone (poly(N-vinyl-2-pyrrolidone); PVP), various chain lengths may be selected each giving various characteristics to the coating. Typically, such polyvinyl pyrrolidone polymers have a number average molecular weight of above 100,000. As an example, PVP K-90 with 1,570,000 in $M_w$, or PVP K-120 with 3,470,000 in $M_w$, can be selected but other types of PVP with other molecular weights may also be used.

In one embodiment, the substrate polymer is polyurethane and the hydrophilic polymer is polyvinylpyrrolidone. In another embodiment, the substrate polymer is polyvinylchloride and the hydrophilic polymer is polyvinylpyrrolidone.

When polyvinylpyrrolidone is the hydrophilic polymer, the molecular weight thereof is preferably at least 50,000, such as at least 100,000, in particular at least 500,000.

In another embodiment, the substrate polymer is polyurethane and the hydrophilic polymer is polyethylene oxide.

When polyethylene oxide is the hydrophilic polymer, the molecular weight thereof is at least 100,000, such as at least 250,000, in particular at least 500,000.

The hydrophilic polymer(s) constitute(s) 0.1-20%, preferably 0.2-15%, such as 0.3-10%, by weight of the polymer solution.

When polyvinylpyrrolidone is the hydrophilic polymer, polyvinylpyrrolidone typically constitutes 1-20%, preferably 2-15%, such as 3-10%, by weight of the polymer solution.

When polyethylene oxide is the hydrophilic polymer, polyethylene oxide typically constitutes 0.1-10%, preferably 0.2-5%, such as 0.3-3%, by weight of the polymer solution.

An important constituent of the vehicle of the polymer solution is the optionally substituted 1,3-dioxolane compound(s) which constitute 50-100%, such as 55-100%, by weight of the vehicle. In some interesting embodiments, the 1,3-dioxolane compound is substantially the sole vehicle constituent.

Apart from 1,3-dioxolane (the unsubstituted 1,3-dioxolane compound), a number of substituted derivatives may be used with good results. Examples of substituted derivatives are 2-dimethylamino-1,3-dioxolane, 2-methyl-1,3-dioxolane, 4-methyl-1,3-dioxolane, and 2-(2-(2-methoxyethoxy)ethoxy)-1,3-dioxolane. It is envisaged that other derivatives including one or several 1,3-dioxolane ring(s) can easily be synthesized from the appropriate (poly)carbonyl compounds and alkylene glycols under acidic conditions, and it is further envisaged that such compounds may be good solvents for hydrophilic polymers and may produce stable hydrophilic coatings. Useful 1,3-dioxolane compounds in the context of the present invention, however, preferably have a molecular weight of less than 300 g/mol.

This being said, 1,3-dioxolane is currently by far the most preferred compound due to its availability and moderate commercial price. Typically, a single 1,3-dioxolane compound is used, however, it is envisaged that two or more 1,3-dioxolane compounds may be used in combination.

The vehicle may also include other solvents and plasticizers in combination with the 1,3-dioxolane compound(s).

Illustrative examples of solvents are 1,4-dioxane and other ethers, acetone, methyl ethyl ketone and other ketones, dimethyl sulfoxide and other sulfoxides, dimethyl formamide and other amides, N-methyl-2-pyrrolidone and other lactams, ethanol and other alcohols, glycols, glycol ethers, glycol esters, other esters, amines, heterocyclic compounds, morpholine and derivatives, alkylated urea derivatives, liquid nitriles, nitroalkanes, haloalkanes such as methylene chloride, haloarenes, trimethyl phosphate, dialkyl alkanephosphonates, and other commonly known organic solvents. The preferred solvents may either be used singly or in combination.

Illustrative examples of plasticizers are acetyl triethyl citrate, dimethyl sulfone, ethylene carbonate, glycerol diacetate, glycerol triacetate, hexamethylphosphoramide, isophorone, methyl salicylate, N-acetyl morpholine, propylene carbonate, quinoline, sulfolane, triethyl citrate, triethyl phosphate and higher phosphate esters, phthalates (e.g. dioctyl phthalate), Santicizers, and adipates (e.g. dioctyl adipate).

Currently preferred solvents and plasticizers are selected from ethanol, N-methyl-2-pyrrolidone, dimethyl sulfoxide, acetone, dimethyl formamide, 1,4-dioxane, methylene chloride, acetyl triethyl citrate, propylene carbonate, sulfolane, glycerol diacetate, glycerol triacetate, and triethyl citrate (Citrofol A1).

Typically, the solvent(s) and/or plasticizers constitute(s) 0-49.9%, e.g. 0-44.8% by weight of the polymer solution.

One or more additives may be included in the polymer solution in order to improve the production of the medical device or the performance of the hydrophilic coating. Additives may be present in a total amount of 0-10% by weight, e.g. 0-5% by weight of the polymer solution.

In one embodiment, the polymer solution consists of:
0.1-20% by weight of the hydrophilic polymer,
55-100% by weight of one or more 1,3-dioxolane compounds,
0-10% by weight of additive(s), and
0-44.9% by weight of solvent(s) and/or plasticizer(s).

In one preferred embodiment, the polymer solution consists of:
1-20% by weight of polyvinyl pyrrolidone as the hydrophilic polymer,
55-100% by weight of a 1,3-dioxolane compound, in particular 1,3-dioxolane,
0-10% by weight of additive(s),
0-44% by weight of solvent(s)/plasticizer(s) selected from the group consisting of ethanol, N-methyl-2-pyrrolidone, dimethyl sulfoxide, acetone, methyl isobutyl ketone, dimethyl formamide, 1,4-dioxane, methylene chloride, acetyl triethyl citrate, propylene carbonate, sulfolane, glycerol diacetate, glycerol triacetate, and triethyl citrate.

In another preferred embodiment, the polymer solution consists of:
0.1-10% by weight of polyethylene oxide as the hydrophilic polymer,
55-100% by weight of a 1,3-dioxolane compound, in particular 1,3-dioxolane,
0-10% by weight of additive(s),
0-44.9% by weight of solvent(s)/plasticizer(s) selected from the group consisting of ethanol, N-methyl-2-pyrrolidone, dimethyl sulfoxide, acetone, methyl isobutyl ketone, dimethyl formamide, 1,4-dioxane, methylene chloride, acetyl triethyl citrate, propylene carbonate, sulfolane, glycerol diacetate, glycerol triacetate, and triethyl citrate.

In some interesting embodiments of the above, the substrate polymer is polyurethane. In further interesting embodiments, the hydrophilic polymer is polyvinyl pyrrolidone. In particular, the substrate polymer is polyurethane and the hydrophilic polymer is polyvinyl pyrrolidone.

Furthermore, the polymer solution may also include polymers other than polyvinylpyrrolidone and polyethylene oxide. In such cases, the amount of such additional polymer should not exceed twice the total amount of the polyvinylpyrrolidone and/or the polyethylene oxide, preferably the amount of such additional polymer should not exceed the total amount of the polyvinylpyrrolidone and/or the polyethylene oxide.

In one intriguing embodiment, the polymer solution comprises polyvinylpyrrolidone and polyurethane (as the additional polymer) in a relative weight ratio of in the range of 99:1 to 1:2, such as in the range of 5:1 to 2:3.

Thus, in a further embodiment, the polymer solution consists of:
1-20% by weight of polyvinyl pyrrolidone as the hydrophilic polymer,
0.05-10% by weight of polyurethane as the additional polymer, where the relative ratio between the polyvinyl pyrrolidone and the polyurethane is in the range of 5:1 to 2:3,
55-100% by weight of a 1,3-dioxolane compound, in particular 1,3-dioxolane,
0-10% by weight of additive(s),
0-43.95% by weight of solvent(s)/plasticizer(s).

Due to the fact that the hydrophilic coating exhibits its advantageous properties when in its non-cross-linked form, it is preferred that the polymer solution is devoid of any cross-linking agents.

The Method Steps

The method of the invention provides a package comprising a medical device element of a substrate polymer having on at least a part of the surface thereof a non-cross-linked hydrophilic coating. The method comprises the following steps (i)-(v) which will be discussed in the following.

Step (i)

In the first step of the method of the invention, a medical device element comprising a substrate polymer selected from the group consisting of polyurethane and polyvinylchloride is provided. The substrate polymer surface may be the native surface of the medical device element, or may be surface treated so as to facilitate strong bonding of the hydrophilic coating to the substrate polymer. The surface of the substrate polymer may be the complete physical surface or a fraction thereof. For many medical devices, it is only necessary to coat the part of the substrate polymer surface that comes into direct contact with the surface of living tissue when in use. Thus, the step of providing a substrate polymer having the substrate polymer surface will be evident for the person skilled in the art.

Step (ii)

In a second step of the method, a polymer solution is provided. The polymer solution comprises 0.1-20% by weight of a hydrophilic polymer selected from the groups consisting of polyvinylpyrrolidone and polyethylene oxide, 0-10% by weight of additive(s), and the balance of a vehicle, said vehicle comprising 50-100% by weight of an optionally substituted 1,3-dioxolane compound, with the proviso that the hydrophilic polymer is not polyethylene oxide when the substrate polymer is polyvinylchloride. The selection of polymer solution is crucial for the method of the invention. The choice of hydrophilic polymer, the 1,3-dioxolane compound, and any solvent(s)/plasticizer(s) and additives are described above. The solution may be prepared by mixing the components of the vehicle with the hydrophilic polymer in order to obtain the polymer solution. The mixing order is not particularly critical as long as a homogeneous (and possibly clear) solution is obtained. Thus, the step of actual preparation of the polymer solution will be evident for the person skilled in the art in view of the above directions with respect to choice of vehicle components.

Step (iii)

In a third step of the method, the polymer solution is applied to the substrate polymer, whereby a non-cross-linked hydrophilic coating is formed on at least a part of the surface thereof. Application of the polymer solution to said substrate polymer surface is conducted following conventional methods such as dip coating, spray coating, application by means of brushes, rollers, etc., as will be evident for the person skilled in the art. With due consideration of the production process, it is preferred that the application of the polymer to the substrate polymer surface is performed by dipping the medical device (or the relevant surface thereof) into the polymer solution.

In a preferred embodiment, the polymer solution is applied to the substrate polymer surface in one single application step, such as in a one-dip process.

In another preferred embodiment, the polymer solution is applied to the substrate polymer surface in two or three individual application steps, in particular in two individual application steps, such as in a two-dip process.

The dipping process typically takes place by immersing the medical device element in the polymer solution and then withdrawing them at a speed of 0.2-10 cm per second at a temperature of in the range of 0-100° C., such as at 1-3 cm per second at room temperature.

For all embodiments, it should be understood that the substrate polymer may be primed in one or more preceding step(s) and that such (a) preceding step(s) may be performed in addition to the before-mentioned application step(s) (e.g. one-dip process or two-dip process) of applying the polymer solution. As mentioned above, the primer coat may be formed from a dilute solution of the polymer solution.

Hence, in a preferred embodiment, the application of the polymer solution (one or two dips, in particular one dip) to the substrate polymer surface (step (iii)) is preceded by a priming step in which a dilute solution of the polymer solution (e.g. using a dilution factor of 0.2-7, and typically diluted with a solvent or a solvent mixture, most typically tetrahydrofuran or ethanol) is applied to the polymer substrate surface in one or more steps (in particular in one step). In particular, both application steps (the priming step and step (iii)) involve dipping of the substrate polymer surface in the primer solution and polymer solution, respectively. More preferred, the priming step and step (iii) are each performed by one dip of the substrate polymer surface (or the relevant part thereof) into the relevant solution (i.e. the primer solution and the polymer solution, respectively).

In some embodiments, the polymer solution is applied to the full (outer) surface of the substrate polymer, and in some other embodiments, only to a part of the surface. In the most relevant embodiments, the coating is established on at least a part of the surface (preferably the whole surface) of the medical device that—upon proper use—comes into direct contact with body parts of the person for which the medical device is intended.

In an alternative embodiment, the polymer solution is applied to the inner surface of a medical device element, e.g. the inner surface of a tube, a catheter, etc. This embodiment provides the advantage that microbial attachment and biofilm formation are avoided and, consequently, that encrustation is eliminated.

In order to ensure that only a part of the substrate surface is coated, a part of the surface of the medical device element may be masked.

Step (iv)

In a fourth step of the method, the vehicle (i.e. the 1,3-dioxolane compound and any solvent(s) and/or plasticizer(s)), or at least a part thereof, is evaporated from the polymer solution present on said substrate polymer surface. The aim is to remove the volatile components of the polymer solution and to ensure that the hydrophilic polymer(s) remain(s) suitably anchored or embedded in the substrate polymer. The volatile components may be removed by passive evaporation, by leading a stream of air over the surface of the substrate polymer, or by applying a reduced pressure over the surface of the substrate polymer. The drying typically takes place at a temperature in the range of 20-100° C. for 1-60 minutes, such as at 70° C. for 30 minutes. Furthermore, it may be necessary or desirable to increase the temperature of the substrate polymer or the air surrounding the substrate polymer to speed up the evaporation process. Preferably, the evaporation process is facilitated by drying the substrate polymer with the polymer solution at a temperature in the range of 25-100° C. depending on the thermostability of the substrate polymer. Typically, the substrate polymer (e.g. a medical device) is dried in an oven.

Step (v)

In a fifth and final step of the method of the invention, the medical device element having the coating of the non-cross-linked hydrophilic polymer is arranged within a packing means, and the packing means is then sealed. An important feature of the invention is the fact that the hydrophilic coating is not cross-linked before sealing, i.e. the packing means holds a medical device element having a coating of a non-cross-linked hydrophilic polymer.

By the term "packing means" is meant a structure intended to enclose other objects, liquids, etc. so as to shield said objects, liquids, etc. from the exterior of the packing means.

Packing means may be prepared from materials like plastics such as polyvinyl chloride (PVC), polyethylene (PE), polypropylene (PP), polyvinylidene difluoride (PVDF), polytetrafluoroethylene (PTFE), rubber such as e.g. synthetic caoutchouc-ethylene-propylene-diene-monomer (EPDM), FKM fluoroelastomer, and paper coated with such polymers and rubbers. Polyethylene is a currently preferred material. The material may be a multi-layered material, e.g. a three-layered foil consisting of polyethyleneterephthalate (PET)/aluminium/polyethylene (PE), where polyethylene is the inner layer that is in direct contact with the medical device element.

The packing means is preferably gas impermeable. The term "gas impermeable" should be understood in this context to mean any material that will be sufficiently tight against diffusion for a period exceeding the recommended shelf life of the assembly which could be up to five years, typically about 36 months or more.

Many designs for the packing means can be envisaged, and examples of packing means particularly suitable for urinary catheters are, e.g., disclosed in EP 0 923 398 and in WO 03/092779. In some embodiments, the packing means in itself forms part of the medical device, i.e. the packing means is a medical device element in itself.

In some instances, the medical device element is arranged within the packing means in wet form, i.e. in swollen form, either by swelling the hydrophilic coating with a swelling medium prior to arrangement within the packing means, or by arranging the medical device within the packing means together with a swelling medium. A suitable swelling medium is, e.g., water or an aqueous solution comprising salts, buffers and/or osmolality increasing agents, and possibly also low-molecular variant of the hydrophilic polymer. With due consideration of the results provided in the Experimental section, it is preferred that the medical device is sterilized in dry form. In the instance where the medical device is prepared from the combination of polyvinylpyrrolidone and polyurethane on a polyurethane substrate, the medical device may also advantageously be sterilized in wet form, in particular swollen with a swelling medium comprising salt and 1-10% of a low-molecular weight polyvinylpyrrolidone.

After sealing of the packing means, the package may afterward be sterilized and shipped as any conventional medical devices.

The present invention—of course—also relates to a package prepared according to the before-mentioned method.

A Medical Device Element

The method defined herein is particularly useful for the preparation of a medical device element comprising a substrate polymer selected from the group consisting of polyurethane and polyvinylchloride, wherein said substrate polymer has on at least a part thereof a coating of a non-cross-linked hydrophilic polymer selected from the group consisting of polyvinylpyrrolidone and polyethylene oxide, with the proviso that the hydro philic polymer is not polyethylene oxide when the substrate polymer is polyvinylchloride, and wherein said hydrophilic coating has a very satisfactory coating stability, and possibly also a fairly long dry-out time.

In one embodiment, the medical device element comprises a polyurethane substrate, said substrate polymer having on at least a part thereof a coating of non-cross-linked polyvinylpyrrolidone, wherein the coating stability of said coating, when determined in the "Coating Stability test" defined herein, being at least 3, such as at least 4, in particular 5. In this embodiment, it is preferred that the polyvinylpyrrolidone has a molecular weight of at least 50,000, such as at least 100,000, in particular at least 250,000.

In another embodiment, the medical device element comprises a polyurethane substrate, said substrate polymer having on at least a part thereof a coating of non-cross-linked polyethylene oxide, wherein the coating stability of said coating, when determined in the "Coating Stability test" defined herein, being at least 3, such as at least 4, in particular 5. In this embodiment, it is preferred that the polyethylene oxide has a molecular weight of at least 100,000, such as at least 250,000, in particular at least 500,000.

In still another embodiment, the medical device element comprises a polyvinylchloride substrate, said substrate polymer having on at least a part thereof a coating of non-cross-linked polyvinylpyrrolidone, wherein the coating stability of said coating, when determined in the "Coating Stability test" defined herein, being at least 3, such as at least 4, in particular 5.

In this embodiment, it is preferred that the polyvinylpyrrolidone has a molecular weight of at least 50,000, such as at least 100,000, in particular at least 250,000.

In the above embodiments, it is further preferred that the dry-out time of said coating, when determined in the "Dry-out time test" defined herein, is at least 3 minutes, such as at least 5 minutes, in particular at least 7 minutes.

The present invention, thus, also provides a package comprising a sealed packing means holding a medical device element as defined above. In particular, the package is prepared according to the method defined herein.

The invention is further illustrated by the following examples.

EXPERIMENTAL

Materials
1,3-dioxolane was from Fluka.
1,4-dioxane was from Riedel-De Haën.
2-methyl-1,3-dioxolane; 4-methyl-1,3-dioxolane, 2-dimethylamino-1,3-dioxolane; and 2-(2-(2-methoxyethoxy)ethoxy)-1,3-dioxolane were from Sigma-Aldrich.
Acetone and ethanol were from VWR International.
Hydroslip and Hydromed TP were from Cardiotech.
Methyl isobutyl ketone and methylene chloride were from Merck.
Polyox 308 (molecular weight (MW)=8.0 MDa), WSR-301 (MW=4.0 MDa), and WSR N-3000 (MW=0.4 MDa) were from Union Carbide.
Propylene carbonate was from J. T. Baker.
PVP C-15, K-25, K-29/32, K-90, and K-120 were from ISP.
Sulfolane was from Aldrich.
Tecogel 500 and Tecogel 2000 (low- and high-molecular type) were from Thermedics.
Triethyl citrate (Citrofol A1) was from Jungbunzlauer.

Dipping Procedure and Drying
CH12 male urinary catheters (diameter 3.8 mm) made from PVC or Estane 58212 polyurethane (PU) were dipped in the coating liquids and withdrawn at 2 cm/s. After drying at 70° C. for 30 minutes, they were ready to use. The catheters were swelled in tap water for at least 30 seconds before measurement of friction, dry-out time, and coating stability.

Friction Measurement
The slippery part of a swelled catheter was placed horizontally between a lower and an upper polished block of stainless steel in such a way that the upper block exerted its full gravitational force on the catheter. The mass and length of the upper steel block was 266 g and 34 mm, respectively. The steel blocks were moved back and forth by a motor, and the push and pull force was measured continuously by a load cell attached to the connector of the catheter. The initial push/pull force was averaged, and the friction force reported was the average of determinations on three separate catheters. A good catheter should have a small friction force.

Dry-out Time Test
5 catheters were withdrawn from the swelling medium at the same time and suspended vertically by the connector in a scaffold, with the slippery part and the eyes pointing downwards. The measurement was made at ambient lab conditions at room temperature, and no attempt was made to control the humidity of the surrounding air. At 5 predetermined time points (typically 1, 3, 5, 7, and 9 minutes) the slipperiness of the catheters was rated on a scale from 0-5 by running two fingers over the catheters from top to bottom: 5=perfectly slippery, 4=slight dryness but still slippery all over, 3 noticeable dryness but still slippery all over, 2 significant dryness with some dry spots, 1=almost completely dry, 0=completely dry. Each catheter was probed only once and then discarded. The rating of the catheters inevitably decreased with time, and the dry-out time was defined as the last time the catheter scored 3 or more. For example, if a catheter scored (5, 5, 3, 2, 1) after (1, 3, 5, 7, 9) minutes, the dry-out time was 5 minutes. If the dry-out time was greater than 9 minutes, then 11 minutes was reported. If the dry-out time was smaller than 1 minute, then 0 minutes was reported. A long dry-out time was desirable.

Coating Stability Test
A catheter was drawn from the swelling medium, and a metal syringe tube almost as long as the catheter was inserted into the catheter lumen to give rigidity. The catheter was then subjected to multiple finger rubbings, first in air and then under lukewarm water, to see if the coating could be rubbed off within a few minutes. The catheters were scored on a scale from 0-5:5=coating was stable for more than 1 minute, 4=coating was stable for 30 to 60 seconds, 3=coating was stable for 15-30 seconds, 2=coating was stable for 5 to 15 seconds, 1=coating could be removed within one or two finger strokes, 0=no coating on the substrate at all. A high score was desirable.

EXAMPLES

Example 1

Effect of Polymer Length on Coating Quality of PU Catheters

PU catheters were dipped in solutions containing equal concentrations of polymers with different molecular weight. The results are shown in Table 1.

TABLE 1

Effect of polymer length on the coating quality of PU catheters.

| Dip # | % PVP K-29/32 | % PVP K-90 | % PVP K-120 | % ethanol | % propylene carbonate | % methylene chloride | % 1,3-dioxo-lane | MW of polymer (g/mol) | Dry-out time (min) | Coating stability | Friction (N) |
|---|---|---|---|---|---|---|---|---|---|---|---|
| 1 |  | 3 |  |  |  |  | 97 | 1.6E+06 | 5 | 5 | 0.224 |
| 2 |  |  | 3 |  |  |  | 97 | 3.5E+06 | 3 | — | 0.169 |
| 3 | 6 |  |  |  |  |  | 94 | 6.7E+04 | 3 | 5 | 1.128 |
| 4 |  | 6 |  |  |  |  | 94 | 1.6E+06 | 9 | — | 0.252 |

TABLE 1-continued

Effect of polymer length on the coating quality of PU catheters.

| Dip # | % PVP K-29/32 | % PVP K-90 | % PVP K-120 | % ethanol | % propylene carbonate | % methylene chloride | % 1,3-dioxolane | MW of polymer (g/mol) | Dry-out time (min) | Coating stability | Friction (N) |
|---|---|---|---|---|---|---|---|---|---|---|---|
| 5 | | | 6 | | | | 94 | 3.5E+06 | 11 | 5 | 0.084 |
| 6 | | 6 | | 28.2 | | | 65.8 | 1.6E+06 | 7 | — | 0.201 |
| 7 | | | 6 | 28.2 | | | 65.8 | 3.5E+06 | 11 | 3 | 0.265 |
| 8 | | 6 | | | 28.2 | | 65.8 | 1.6E+06 | 7 | 5 | 0.792 |
| 9 | | | 6 | | 28.2 | | 65.8 | 3.5E+06 | 11 | 5 | 0.257 |
| 10 | | 6 | | | | 28.2 | 65.8 | 1.6E+06 | 5 | 5 | 0.913 |
| 11 | | | 6 | | | 28.2 | 65.8 | 3.5E+06 | 11 | 5 | 0.211 |

The dry-out time increased and the friction decreased in almost all cases when the molecular weight of the polymer was increased. Hence, longer polymers gave better coatings.

Example 2

Effect of Polymer Concentration on Coating Quality of PU Catheters

PU catheters were dipped in solutions with different concentrations of the same polymer. The results are shown in Table 2.

TABLE 2

Effect of polymer concentration on the coating quality of PU catheters.

| Dip # | % WSR N-3000 | % PVP K-90 | % PVP K-120 | % 1,3-dioxolane | Dry-out time (min) | Coating stability | Friction (N) |
|---|---|---|---|---|---|---|---|
| 12 | 1 | | | 99 | 3 | — | 0.38 |
| 13 | 3 | | | 97 | 7 | — | 0.369 |
| 1 | | 3 | | 97 | 5 | 5 | 0.224 |
| 4 | | 6 | | 94 | 9 | — | 0.252 |
| 2 | | | 3 | 97 | 3 | — | 0.169 |
| 5 | | | 6 | 94 | 11 | 5 | 0.084 |

In all cases, the dry-out time increased with increasing polymer concentration, that is, a thick polymer layer protected better against water evaporation than a thin one. Furthermore, in most cases the friction decreased with increasing polymer concentration.

Example 3

Effect of Addition of Various Solvents on the Coating Quality of PU Catheters PU catheters were dipped in solutions with different solvents in addition to 1,3-dioxolane. The results are shown in Table 3.

TABLE 3

Effect of various solvents on the coating quality of PU catheters.

| Dip # | % WSR-301 | % Polyox 308 | % PVP K-90 | % PVP K-120 | Other | % sulfolane | % 1,4-dioxane | % methylene chloride | % acetone | % propylene carbonate | % 1,3-dioxolane | Dry-out time (min) | Coating stability | Friction (N) |
|---|---|---|---|---|---|---|---|---|---|---|---|---|---|---|
| 14 | 1 | | | | | 29.7 | | | | | 69.3 | 11 | — | 0.089 |
| 15 | 1 | | | | | | 19.8 | | | | 79.2 | 11 | 3 | 0.141 |
| 16 | 1 | | | | | | | 29.7 | | | 69.3 | 11 | — | 0.26 |
| 17 | 1 | | | | | | | | 29.7 | | 69.3 | 11 | — | 0.313 |
| 18 | 1 | | | | 19.8% methyl isobutyl ketone | | | | | | 79.2 | 11 | 2 | 0.341 |
| 19 | 1 | | | | 99% 4-methyl-1,3-dioxolane | | | | | | 0 | 11 | — | 0.429 |
| 20 | 1 | | | | 99% 2-methyl-1,3-dioxolane | | | | | | 0 | 11 | — | 0.481 |
| 21 | | 0.3 | | | | | | | | | 99.7 | 5 | 5 | 0.282 |
| 6 | | | 6 | | 28.2% ethanol | | | | | | 65.8 | 7 | — | 0.201 |
| 4 | | | 6 | | | | | | | | 94 | 9 | — | 0.252 |
| 8 | | | 6 | | | | | 28.2 | | | 65.8 | 7 | 5 | 0.792 |
| 10 | | | 6 | | | | | 28.2 | | | 65.8 | 5 | 5 | 0.913 |
| 22 | | | | 6 | | 18.8 | | | | | 75.2 | 11 | 3 | 0.074 |
| 5 | | | | 6 | | | | | | | 94 | 11 | 5 | 0.084 |
| 23 | | | | 6 | 94% 2-dimethylamino-1,3-dioxolane | | | | | | 0 | 11 | — | 0.115 |
| 24 | | | | 6 | 28.2 | | | | | | 65.8 | 11 | 5 | 0.144 |
| 25 | | | | 6 | | | | 28.2 | | | 65.8 | 11 | 5 | 0.2 |
| 11 | | | | 6 | | | | 28.2 | | | 65.8 | 11 | 5 | 0.211 |
| 9 | | | | 6 | | | | | | 28.2 | 65.8 | 11 | 5 | 0.257 |
| 26 | | | | 6 | 94% 2-(2-(2-methoxyethoxy)-ethoxy)-1,3-dioxolane | | | | | | 0 | — | 5 | — |
| 7 | | | | 6 | 28.2% ethanol | | | | | | 65.8 | 11 | 3 | 0.265 |

The data were ordered by increasing friction in each group. In general, coatings with low friction were obtained when sulfolane or 1,4-dioxane were added, or when neat 1,3-dioxolane was used. Coatings resulting from addition of acetone and methylene chloride generally had somewhat higher friction than coatings with neat 1,3-dioxolane. Coatings with propylene carbonate, methyl isobutyl ketone and ethanol generally gave coatings with even higher frictions.

With 0.3% Polyox 308 the coating with neat 1,3-dioxolane was completely stable (dip # 21), even though the dry-out time and friction were not particularly good. Hence, neat 1,3-dioxolane was a good solvent for the manufacture of hydrophilic coatings Neat 4-methyl-1,3-dioxolane and 2-methyl-1,3-dioxolane gave coatings with good dry-out times and frictions that, even though they came out last, were not much larger than the frictions of the other solvents in the group with 1% WSR-301. Hence, these two derivatives of 1,3-dioxolane gave coatings with good properties. Neat 2-dimethylamino-1,3-dioxolane gave a low friction and a high dry-out time with 6% PVP K-120 and was also a very interesting solvent. Dry-out time and friction were not measured for 6% PVP K-120 in neat 2-(2-(2-methoxyethoxy)ethoxy)-1,3-dioxolane, but the coating was very stable and had low friction during repeated finger rubbings under running water (data not shown), so this was a useful solvent as well.

Example 4

Effect of β-sterilization on Coating Quality of PU Catheters

PU catheters were coated with dip solution # 4 and subjected to 50 kGy electron beam irradiation (β-irradiation) to see how this affected the coating quality. The results are shown in Table 4.

TABLE 4

Effect of 50 kGy β-irradiation on the coating quality of PU catheters.

| Dip # | % PVP K-90 | % 1,3-dioxolane | Unsterilized PU Friction (N) | Unsterilized PU Coating stability | PU sterilized dry Friction (N) | PU sterilized dry Dry-out time (min) | PU sterilized in 0.9% NaCl Friction (N) | PU sterilized in 0.9% NaCl Dry-out time (min) | PU sterilized in 0.9% NaCl + 6% PVP C-15 Friction (N) | PU sterilized in 0.9% NaCl + 6% PVP C-15 Dry-out time (min) |
|---|---|---|---|---|---|---|---|---|---|---|
| 4 | 6 | 94 | 0.149 | 5 | 0.297 | 8 | 1.134 | 2 | 1.577 | 4 |

The friction of the coating increased somewhat upon dry sterilization but was still acceptable, but the coating did not withstand wet sterilization in isotonic salt water with or without 6% PVP C-15 added.

Example 5

Properties of Stored and Unstored PVC Catheters

Properties of PVC catheters coated with various dip solutions are shown in Table 5.

TABLE 5

Properties of dip coated PVC catheters.

| Dip # | % PVP K-120 | % PVP K-90 | Other | % 1,3-dioxolane | Unstored PVC Dry-out time (min) | Unstored PVC Coating stability | Unstored PVC Friction (N) | PVC stored 67 hrs. in water at 60 deg. C. Dry-out time (min) | PVC stored 67 hrs. in water at 60 deg. C. Coating stability | PVC stored 67 hrs. in water at 60 deg. C. Friction (N) |
|---|---|---|---|---|---|---|---|---|---|---|
| 5 | 6 | | | 94 | 11 | 5 | 0.169 | 7 | 5 | 0.25 |
| 9 | 6 | | 28.2% propylene carbonate | 65.8 | 11 | 5 | 0.265 | 5 | 5 | 0.148 |
| 11 | 6 | | 28.2% methylene chloride | 65.8 | 11 | 5 | 0.305 | 3 | 5 | 0.42 |
| 24 | 6 | | 28.2% sulfolane | 65.8 | 7 | 5 | 0.541 | 3 | 5 | 0.238 |
| 25 | 6 | | 28.2% acetone | 65.8 | — | 4 | — | — | — | — |
| 8 | | 6 | 28.2% propylene carbonate | 65.8 | — | 4 | — | — | — | — |
| 10 | | 6 | 28.2% methylene chloride | 65.8 | — | 4 | — | — | — | — |
| 4 | | 6 | | 94 | — | 3 | — | — | — | — |

Only results with PVP K-120 and PVP K-90 were included here, because all coatings with polyethylene oxide and PVP K-29/32 were unstable (data not shown).

6% PVP K-120 in neat 1,3-dioxolane gave very good, stable coatings, both before and after storage in water. Coatings with added propylene carbonate, methylene chloride and sulfolane were also stable and almost as good, whereas addition of acetone made the coating slightly unstable. Coatings with 6% PVP K-90 in either neat 1,3-dioxolane or with added propylene carbonate or methylene chloride were reasonably stable. Hence the same effect of molecular weight of the polymer was observed for PVC and PU, but different additional solvents must be used for PU and PVC, and polyethylene oxide could not be coated on PVC with this dipping method.

After storage in hot water for 67 hours, the dry-out time of the PVC catheters decreased, but the coatings were stable. By contrast, all coated PU catheters lost their coating during storage at the same conditions, so the PVC catheter coatings were inherently more stable in water than PU catheter coatings.

Example 6

Properties of Sterilized and Unsterilized PU Catheters Coated with PVP/Polyurethane Mixtures The properties of such catheters are shown in Table 6. In all cases, 50 kGy β-irradiation was used for sterilization.

In general, the dry sterilization did not affect the catheters as much as the wet sterilization in 0.9% NaCl. However, the presence of 6% PVP C-15 in the salt water improved both the dry-out time and the friction and hence would be advantageous for the manufacturing of a wet catheter.

The coating that contained 4% Hydroslip polyurethane and 5% PVP K-90 (dip # 27) had the best all-round properties of the PU-coated catheters: Low friction and a long dry-out time before and after sterilization. The presence of Citrofol A1 as plasticizer for the polyurethane damaged the catheters during wet sterilization (dip # 28), but further addition of 0.95% Hydromed TP almost circumvented the deleterious effect of Citrofol A1 after wet sterilization (dip # 29). However, a poor coating resulted when PVP K-90 was replaced by PVP K-25 (dip # 30). On the other hand, Hydromed TP gave almost equally good results with PVP K-90 (dip # 31) and PVP K-25 (dip # 32). The high-molecular weight version of Tecogel 2000 (dip # 33) gave coatings with better dry-out times than the low-molecular weight Tecogel 2000 (dip # 34), in thread with the observations described above for PU-free coatings containing only PVP or polyethylene oxide. None of the pure polyurethanes (that is, without PVP) were very good, as exemplified by the pure low-molecular weight Tecogel 2000 (dip # 35; other data not shown). Finally, the coating from a mixture of Tecogel 500 with PVP K-25 and Citrofol A1 (dip

TABLE 6

Properties of sterilized and unsterilized PU catheters coated with PVP/polyurethane mixtures.

| Dyp # | % PVP K-90 | % PVP K-25 | PU type | Other | % Citrofol A1 | % 1,3-dioxo-lane |
|---|---|---|---|---|---|---|
| 27 | 5 | | 4% Hydroslip | | | 91 |
| 28 | 4.75 | | 3.8% Hydroslip | | 5 | 86.45 |
| 29 | 4.75 | | 3.8% Hydroslip | 0.95% Hydromed TP | 5 | 85.5 |
| 30 | | 4.75 | 4.75% Hydroslip | | 5 | 85.5 |
| 31 | 5 | | 5% Hydromed TP | | | 90 |
| 32 | | 4.75 | 4.75% Hydromed TP | | 5 | 85.5 |
| 33 | | 4.75 | 4.75% Tecogel 2000 | | 5 | 85.5 |
| 34 | | 5 | 5% Tecogel 2000 (low MW) | | | 90 |
| 35 | | | 5% Tecogel 2000 (low MW) | | | 95 |
| 36 | | 5.7 | 3.8% Tecogel 500 | | 5 | 85.5 |
| 37 | 5 | | 4% Tecogel 500 | 13.65% ethanol | | 77.35 |

| | Unsterilized PU | | PU sterilized dry | | PU sterilized in 0.9% NaCl | | PU sterilized in 0.9% NaCl + 6% PVP C-15 | |
|---|---|---|---|---|---|---|---|---|
| Dyp # | Coating stability | Friction (N) | Dry-out time (min) | Friction (N) | Dry-out time (min) | Friction (N) | Dry-out time (min) | Friction (N) |
| 27 | 5 | 0.22 | 10 | 0.11 | 6 | 0.27 | 10 | 0.11 |
| 28 | 5 | 0.23 | 10 | 0.12 | 2 | 3.14 | 4 | 0.15 |
| 29 | 5 | 0.26 | 4 | 0.19 | 6 | 0.35 | 8 | 0.17 |
| 30 | 5 | 0.94 | 8 | 0.2 | 6 | 1.51 | 4 | 1.43 |
| 31 | 4 | 0.21 | 8 | 0.23 | 2 | 0.55 | 4 | 0.36 |
| 32 | 5 | 0.24 | 4 | 0.28 | 2 | 0.54 | 6 | 0.28 |
| 33 | 5 | 0.22 | 8 | 0.17 | 6 | 0.47 | 8 | 0.33 |
| 34 | 3 | 0.15 | 6 | 0.13 | 2 | 0.61 | 4 | 0.17 |
| 35 | 4 | 0.85 | 2 | 0.32 | 2 | 1.2 | 2 | 0.4 |
| 36 | 3 | 0.19 | 6 | 0.19 | 4 | 0.55 | 8 | 0.21 |
| 37 | 3 | 0.32 | 4 | 0.29 | 2 | 0.35 | 6 | 0.52 |

36) was almost as good as the corresponding dip #33 with Tecogel 2000. Furthermore, dip #36 was better than dip #37 with 5% PVP K-90, 4% Tecogel 500 and 13.65% ethanol, so PVP K-25 sometimes worked better with polyurethanes than PVP K-90. In conclusion, several polyurethanes could be advantageously used to fortify the PVP coating during wet β-sterilization, since PVP alone did not withstand this treatment (see Example 4 above).

The invention claimed is:

1. A method for the preparation of a sealed package for holding a medical device element of a substrate polymer, said substrate polymer having on at least a part of the surface thereof a hydrophilic coating, said method comprising the steps of:
    (i) providing a medical device element having a substrate polymer selected from the group consisting of polyurethane and polyvinylchloride,
    (ii) providing a polymer solution including 0.1-20% by weight of a hydrophilic polymer selected from the group consisting of polyvinylpyrrolidone and polyethylene oxide, 0-10% by weight of additive(s), and the balance of a vehicle having 50-100% by weight of an unsubstituted or substituted 1,3-dioxolane compound, with the proviso that the hydrophilic polymer is not polyethylene oxide when the substrate polymer is polyvinylchloride,
    (iii) applying said polymer solution to the surface of said substrate polymer, thereby forming a non-cross-linked hydrophilic coating on at least a part of the surface of the substrate polymer,
    (iv) evaporating at least a part of the vehicle, and
    (v) arranging said medical device element having the coating of the non-cross-linked hydrophilic polymer within a packing means, and sealing said packing means.

2. The method according to claim 1, wherein the substrate polymer is polyurethane and the hydrophilic polymer is polyvinylpyrrolidone.

3. The method according to claim 1, wherein the substrate polymer is polyvinylchloride and the hydrophilic polymer is polyvinylpyrrolidone.

4. The method according to claim 1, wherein the substrate polymer is polyurethane and the hydrophilic polymer is polyethylene oxide.

5. The method according to claim 1, wherein said unsubstituted or substituted 1,3-dioxolane compound has a molecular weight of at the most 300 g/mol.

6. The method according to claim 1, wherein said unsubstituted or substituted 1,3-dioxolane compound is unsubstituted 1,3-dioxolane.

* * * * *